United States Patent [19]

Ohgomori et al.

[11] Patent Number: 5,254,742

[45] Date of Patent: Oct. 19, 1993

[54] PROCESS FOR PREPARING 2-HEXENE-1,6-DIAL

[75] Inventors: Yuji Ohgomori; Shuji Ichikawa; Takahiro Yoneyama; Naoko Sumitani, all of Ibaraki, Japan

[73] Assignee: Mitsubishi Petrochemical Co., Ltd., Tokyo, Japan

[21] Appl. No.: 958,091

[22] Filed: Oct. 8, 1992

[30] Foreign Application Priority Data

Oct. 8, 1991 [JP] Japan .................................. 3-260846
Jan. 8, 1992 [JP] Japan ...................................... 4-1544

[51] Int. Cl.$^5$ ............................................. C07C 45/72
[52] U.S. Cl. ................................... 568/463; 568/459; 568/461
[58] Field of Search ................ 568/461, 463, 458, 459

[56] References Cited

U.S. PATENT DOCUMENTS 3,450,769  6/1969  Payne ................................ 568/461
4,740,639  4/1988  Beavers ............................. 568/461
5,162,552 11/1992  Merger ............................. 568/461

*Primary Examiner*—Werren B. Lone
*Attorney, Agent, or Firm*—Oblon, Spivak, McClelland, Maier & Neustadt

[57] ABSTRACT

A process for preparing 2-hexene-1,6-dial comprising dimerizing 2-propenal in the presence of an organometallic compound of the group VIII metal. The desired compound can be obtained under mild conditions with industrial advantages.

12 Claims, No Drawings

PROCESS FOR PREPARING 2-HEXENE-1,6-DIAL

FIELD OF THE INVENTION

This invention relates to a process for preparing 2-hexene-1,6-dial useful as an intermediate for synthetic resins and various organic compounds such as pharmaceuticals and agricultural chemicals.

BACKGROUND OF THE INVENTION

It has been reported that 2-hexene-1,6-dial is obtained by reacting 1,3-cyclohexadiene with ozone and dimethyl sulfide (see T. Hudlicky et al., *Journal of the American Chemical Society*, Vol. 110, p. 4735 (1988)). However, the process must be carried out by using an expensive raw material in an extremely low concentration while controlling the ozone concentration at $-78°$ C. and is not therefore deemed suitable for industrial production.

On the other hand, generally known processes for dimerizing an olefin having an electron-withdrawing substituent in a tail-to-tail fashion include a process for obtaining dimethyl dihydromuconate which comprises dimerizing an acrylic ester by using, as a catalyst, a ruthenium (see R. J. McKinney et al., *Organometallics*, Vol. 5, p. 1080 (1986)), a ruthenium or palladium compound (see U.S. Pat. No. 3,013,066), or rhodium (see M. Brookhart et al., *Journal of the American Chemical Society*, Vol. 133, p. 2777 (1991)); and a process for obtaining 1,4-dicyano-1-butene which comprises dimerizing acrylonitrile by using, as a catalyst, a ruthenium compound (see JP-A-44-24585, the term "JP-A" as used herein means an "unexamined published Japanese patent application") or an organophosphorus compound (see JP-A-55-98149).

It is also known that dimerization of 2-propenal (1-propen-3-al) at 185° to 195° C. in the absence of a catalyst yields 2,3-dihydro-2-formylpyran (see JP-B-40-9264; the term "JP-B" as used herein means an "examined published Japanese patent application"). Further, it is reported that polymerization of 2-propenal proceeds in the presence of a ruthenium compound as a catalyst (see S. Komiya et al, *Bulletin of the Chemical Society of Japan*, Vol. 48, p. 101 (1975)), but the paper gives no reference to dimerization of 2-propenal.

SUMMARY OF THE INVENTION

An object of the present invention is to provide an industrially advantageous process for preparing 2-hexene-1,6-dial.

The present invention relates to a process for preparing 2-hexene-1,6-dial comprising dimerizing 2-propenal in the presence of a catalyst for dimerization.

DETAILED DESCRIPTION OF THE INVENTION

2-Propenal which is used as a starting compound in the present invention is easily prepared by dehydrating glycerin with a desiccant, such as potassium hydrogensulfate and magnesium sulfate. It may also be obtained quantitatively by oxidizing propene in a gaseous phase in the presence of metallic catalysts.

2-Propenal is so reactive that it is easily oxidized in air or undergoes polymerization during long-term preservation to form a resinous substance.

Dimerization of 2-propenal according to the present invention is carried out by using a catalyst. The catalyst for dimerization to be used includes organometallic compounds comprising at least one of the group VIII metal elements. The group VIII metal elements preferably include iron, ruthenium, and osmium, with ruthenium being particularly preferred.

The group VIII metal is preferably used in the form of an organometallic compound soluble in the starting material. Organic groups to be coordinated or bonded to the group VIII metal include those derived from alkenes, e.g., ethene and butene; dienes, e.g., butadiene, 1,3-cyclohexadiene, 1,4-cyclohexadiene, 1,3-cyclooctadiene, 1,5-cyclooctadiene, and 2,5-norbornadiene; trienes, e.g., 1,3,5-cyclooctatriene; and aromatic hydrocarbon compounds, e.g., benzene, toluene, xylene, cumene, p-cymene, hexamethylbenzene, naphthalene, anthracene, benzonitrile, and anisole. The organic group can be coordinated or bonded to the group VIII metal in the ratio of generally not more than 6 moles and preferably from 1 to 5 moles per 1 mole of the group VIII metal. The amount ratio by mole of the organic group to the organometallic compound to be added in the reaction system is not more than 1,000,000 and preferably not more than 100,000.

Specific examples of the organoruthenium compound are ($\eta^4$-cyclooctadiene)($\eta^6$-cyclooctatriene)ruthenium, ($\eta^6$-benzene)($\eta^4$-1,3-cyclohexadiene)ruthenium, bis(ethene)($\eta^6$-hexamethylbenzene)ruthenium, ($\eta^4$-cyclooctadiene)($\eta^6$-hexamethylbenzene)ruthenium, ($\eta^6$-benzene)($\eta^4$-cyclooctadiene)ruthenium, ($\eta^6$-benzene)($\eta^4$-norbornadiene)ruthenium, ($\eta^4$-cyclooctadiene)($\eta^6$-1,3,5-trimethylbenzene)ruthenium, ($\eta^4$-norbornadiene)($\eta^6$-1,3,5-trimethylbenzene)ruthenium, ($\eta^4$-cyclootakiene)($\eta^6$-toluene)ruthenium, ($\eta^4$-cyclooctadiene)($\eta^6$-xylene)ruthenium, ($\eta^6$-p-cymene)($\eta^4$-cyclooctadiene)ruthenium, ($\eta^4$-cyclooctadiene)($\eta^6$-p-methoxybenzene)ruthenium, ($\eta^4$-cyclooctadiene)($\eta^6$-cycloheptatriene)ruthenium, ($\eta^4$-cycloheptadiene)($\eta^6$-cycloheptatriene)ruthenium, bis(cyclohexadienyl)ruthenium, and bis(hexamethylbenzene)ruthenium.

The organometallic compound of the group VIII metal element may be prepared in situ in the reaction system.

The catalyst is used at a molar ratio of generally from 0.0000001 to 1, preferably from 0.000001 to 0.1, and more preferably from 0.00001 to 0.05, to the starting 2-propenal.

The spent catalyst can be separated from the reaction mixture by general means, such as distillation and extraction, and reused.

While the reaction may be carried out in the absence of a solvent, the reaction may be carried out in an appropriate solvent inert to 2-propenal, if desired. Examples of suitable solvents include water; hydrocarbons, such as hexane, benzene, and toluene; ethers, such as diethyl ether, dimethoxyethane, tetrahydrofuran, and dioxane; esters, such as ethyl acetate, butyl acetate, and butyrolactone; amides, such as dimethylformamide, dimethylacetamide, and N-methylpyrrolidinone; ureas, such as dimethylimidazolidinone and tetramethylurea; and alcohols, such as isopropanol and t-butanol.

Rate to 2-hexene-1,6-dial formation can be increased by adding cyclooctadienes to the reaction mixtures. Ruthenium compounds possessing cyclooctadiene ligands are preferably effective catalysts for 2-hexene-1,6-dial formation. However, the rate may decrease during the dimerization reaction, due to dissociating the cyclooctadiene ligands from ruthenium compounds. Decreasing the catalytic activities can be avoided by carrying out the reaction in the presence of cyclooctadienes. Examples of cyclooctadienes include 1,3-cyclooctadiene, 1,4-cyclooctadiene, 1,5-cyclooctadiene, 1,5-dimethyl-1,5-cyclooctadiene, and mixtures thereof. Molar ratio of adding cyclooctadiene to a catalyst is usually 1 or more, and preferably 10 or more. Of course, cyclooctadienes can be used as the reaction solvents.

When any solvent is used, the 2-propenal concentration is at least 1% by weight, and preferably at least 10% by weight.

While the reaction sufficiently proceeds at below room temperature, the reaction system may be heated to increase the reaction rate. The reaction temperature usually ranges from 0° to 200° C., and preferably from 20° to 150° C. The reaction may be performed in air unless the catalyst undergoes any change but is usually carried out in an oxygen-free atmosphere, i.e., in an evacuated chamber or in a chamber purged with an inert gas, e.g., nitrogen or argon. The reaction pressure usually ranges from 1 to 200 bar, though depending on the reaction temperature.

The reaction rate may further be increased by conducting the reaction in a hydrogen atmosphere. The hydrogen pressure usually ranges from 0.1 to 200 bar, and preferably from 0.5 to 100 bar, though varying depending on the other reaction conditions, such as temperature. Hydrogen to be introduced does not need to have a high purity and may contain other gaseous substances, such as nitrogen, argon, and methane, at an arbitrary ratio to hydrogen.

The reaction time depends on the reaction temperature employed but is usually in the range of from 0.1 to 200 hours, and preferably from 0.5 to 100 hours.

The reaction product obtained may sometimes contain, in addition to 2-hexene-1,6-dial as desired, the isomer of 2-hexene-1,6-dial (i.e., 2-methylenepentane-1,5-dial) or tri- or higher oligomers of 2-propenal. The 2-hexene-1,6-dial produced can be isolated from the reaction mixture containing the catalyst by any known means, such as distillation, extraction, and adsorption.

According to the present invention, 2-hexene-1,6-dial can be obtained from 2-propenal under mild conditions with industrial advantages.

2-Hexene-1,6-dial can be derived to 1,6-hexanediol, adipic acid, or 1,6-hexanediamine, which are starting materials for polyesters or polyamides, through hydrogenation, oxidation, or reductive amination.

In the above precursors for polymers, 1,6-hexanediamine may be the most valuable compound. Production of this compound can be performed by selective hyirogenation of the carbon to carbon double bond of 2-hexene-1,6-dial to form 1,6-hexanedial,and subsequent reductive amination.

The former reaction is carried out in the presence of hydrogenation catalysts usually used in hydrogenation of alkenes. Examples of the catalysts include platinum group elements, such as platinum, palladium, ruthenium, and rhodium, as a metallic state, or as anchored form on a usual support, such as carbon, silica, alumina, silica-alumina, zirconia, magnesia or kieselguhr. Range for weight percentages of a metal on a supported catalyst lies between 0.1 and 20, and preferably between 0.5 and 20. Weight ratio of a catalyst to 2-hexene-1,6-dial ranges usually from 0.00001 to 1, and preferably from 0.0001 to 0.1.

The hydrogenation reaction can be conducted without any solvents, however, compounds inert to 2-hexene-1,6-dial can be used as the solvents when required. Examples of the solvents include aliphatic hydrocarbons, such as hexane and octane; aromatic hydrocarbons, such as benzene and toluene; ethers, such as tetrahydrofuran and dioxane; alcohols, such as methanol and ethanol; esters, such as ethyl acetate and butyl acetate; and water. The reaction is performed in solutions ranging in concentration from 0.1 to 100 wt %, and preferably from 1 to 100 wt %.

The reaction temperature ranges from −50° to 200° C., and preferably from −5° to 100° C. Hydrogen pressure ranges from 1 to 100 bar, and preferably from 1 to 50 bar.

The present invention is now illustrated in greater detail with reference to Reference Examples and Examples, but it should be understood that the present invention is not construed as being limited thereto.

2-Propenal used as a starting material in all the Examples contains 0.1 wt % hydroquinone.

In the Example 10, the reaction mixture was subjected to distillation to remove low-boiling substances, such as the unreacted starting compound, and the dimerization product was then isolated by Kugelrohr distillation. Identification of the thus isolated dimerization product was made by comparing the IR, NMR, and MS spectra of the product with those of 2-hexene-1,6-dial synthesized by a known process comprising oxidation of 1,3-cyclohexadiene with ozone.

Further, the resulting product was quantitatively analyzed by gas chromatography according to an internal standard method. Diethylene glycol dimethyl ether was used as an internal standard substance. A conversion and a selectivity were calculated according to the following equations:

$$\text{Conversion (\%)} = \frac{\text{Mol Number of 2-Propenal Reacted}}{\text{Mol Number of 2-Propenal Charged}} \times 100$$

$$\text{Selectivity (\%)} = \frac{\text{Mol Number of 2-Hexene-1,6-dial Produced} \times 2}{\text{Mol Number of 2-Propenal Reacted}} \times 100$$

Since a pure 2-hexene-1,6-dial sample to be used for preparing a calibration curve is hardly obtainable either on the market or by the above-described known synthetic process, the product obtained in the Examples and purified by distillation was used with its purity determined by $^1$H-NMR analysis.

REFERENCE EXAMPLE 1

Preparation of
($\eta^4$-Cyclooctadiene)($\eta^6$-cyclooctatriene)Ruthenium

All the following operations were conducted in a nitrogen stream.

A 100 ml volume glass flask equipped with a reflux condenser and a dropping funnel was purged with nitrogen, and 12 g of zinc powder, 25 ml of 1,5-cyclooctadiene, and 10 ml of methanol were charged therein. While stirring the contents at 70° C. by ultrasonic waves, 10 ml of a methanol solution of ruthenium trichloride trihydrate (ruthenium trichloride content: 1.06 g) was added thereto dropwise through the dropping funnel over a period of 1 hour. After the addition, the ultrasonic stirring was further continued at 70° C. for an additional period of 5 hours. The reaction mixture was cooled to room temperature and filtered to remove any solid, and the filtrate was distilled under reduced pressure to remove methanol and the unreacted 1,5-cyclooctadiene. The residue was extracted from three 8-ml portions of hexane, the extract was placed on an alumina column. Chromatographic separation was done with hexane as an eluent, and a yellow band was collected. The yellow solution was concentrated and cooled on a dry ice-acetone bath to obtain 0.64 g of orange needle crystals. The yield based on ruthenium trichloride trihydrate was 50%.

REFERENCE EXAMPLE 2

Preparation of ($\eta^4$-Cyclooctadiene)($\eta^6$-Toluene)Ruthenium

A 25 ml-volume Schlenk flask having a stirrer in it was purged with nitrogen, and 0.6522 g (2.07 mmol) of ($\eta^4$-cyclooctadiene)($\eta^6$-cyclooctatriene)ruthenium was dissolved in a 10 ml of toluene. A balloon containing hydrogen was fixed to the flask, and the solution was stirred at room temperature for 5 hours, followed by filtration through Celite. The filtrate was distilled under reduced pressure to remove unreacted toluene to obtain a yellow powder. The powder was dissolved in pentane, and the solution was cooled on a dry ice-acetone bath to obtain 0.5542 g (1.84 mmol) of yellow needle crystals. The yield based on the starting ($\eta^4$-cyclooctadiene)($\eta^6$-cyclooctatriene)ruthenium was 89%.

REFERENCE EXAMPLE 3

Preparation of ($\eta^6$-Benzene)($\eta^4$-Cyclooctadiene)Ruthenium

The same procedures as in Reference Example 2 were followed, except for using 0.8109 g (2.57 mmol) of ($\eta^4$-cyclooctadiene)($\eta^6$-cyclooctatriene)ruthenium and replacing toluene with benzene. As a result, there was obtained 0.6253 g (2.18 mmol) of ($\eta^6$-benzene)($\eta^4$-cyclooctadiene)ruthenium. The yield based on the starting ($\eta^6$-cyclooctadiene)($\eta^4$-cyclooctatriene)ruthenium was 85%.

EXAMPLE 1

In a 5 ml-volume glass ampule containing a magnetically stirring bar were charged 61.2 mg (0.19 mmol) of ($\eta^4$-cyclooctadiene)($\eta^6$-cyclooctatriene)ruthenium, 2.14 g (38.17 mmol) of 2-propenal, and, as an internal standard substance for analysis, 0.22 g of diethylene glycol dimethyl ether in a nitrogen stream. After sealing the ampule, the contents were allowed to react at room temperature for 90 hours while stirring. After completion of the reaction, the reaction mixture was found to contain 0.837 g (14.93 mmol) of 2-propenal and 0.223 g (1.99 mmol) of (Z)-2-hexene-1,6-dial. In addition, tri- or higher oligomers of 2-propenal were also detected. The conversion of 2-propenal was 61.0%, and the selectivity to (Z)-2-hexene-1,6-dial was 17.1%.

EXAMPLE 2

The same procedures as in Example 1 were followed, except for changing the reaction conditions to 70° C.×3 hours. As a result, the reaction mixture was found to contain 0.517 g (9.22 mmol) of 2-propenal and 0.393 g (3.50 mmol) of (Z)-2-hexene-1,6-dial. In addition, tri- or higher oligomers of 2-propenal were also detected. The conversion of 2-propenal was 75.8%, and the selectivity to (Z)-2-hexene-1,6-dial was 24.2%.

EXAMPLE 3

The same procedures as in Example 2 were followed, except for using 0.936 g (16.70 mmol) of 2-propenal and 0.085 g of diethylene glycol dimethyl ether and replacing ($\eta^4$-cyclooctadiene)($\eta^6$-cyclooctatriene)ruthenium with 24.4 mg (0.09 mmol) of ($\eta^6$-benzene)($\eta^4$-cyclooctadiene)ruthenium. As a result, the reaction mixture was found to contain 0.178 g (3.17 mmol) of 2-propenal and 0.233 g (2.08 mmol) of (Z)-2-hexene-1,6-dial. In addition, tri- or higher oligomers of 2-propenal were also detected. The conversion of 2-propenal was 81.0%, and the selectivity to (Z)-2-hexene-1,6-dial was 30.7%.

EXAMPLE 4

The same procedures as in Example 2 were followed, except for using 0.931 g (16.61 mmol) of 2-propenal, 27.2 mg (0.09 mmol) of ($\eta^4$-cyclooctadiene)($\eta^6$-cyclooctatriene)ruthenium, and 0.097 g of diethylene glycol dimethyl ether and additionally using 48 mg (0.3 mmol) of hexamethylbenzene. As a result, the reaction mixture was found to contain 0.186 g (3.32 mmol) of 2-propenal and 0.171 g (1.53 mmol) of (Z)-2-hexene-1,6-dial. In addition, tri- or higher oligomers of 2-propenal were also detected. The conversion of 2-propenal was 80.0%, and the selectivity to (Z)-2-hexene-1,6-dial was 23.0%.

EXAMPLE 5

The same procedures as in Example 2 were followed, except for using 1.712 g (30.54 mmol) of 2-propenal, 30.0 mg (0.10 mmol) of ($\eta^4$-cyclooctadiene)($\eta^6$-cyclooctatriene)ruthenium, and 0.17 g of diethylene glycol dimethyl ether and additionally using 0.86 ml of toluene. As a result, the reaction mixture was found to contain 0.762 g (13.59 mmol) of 2-propenal and 0.230 g (2.05 mmol) of (Z)-2-hexene-1,6-dial. In addition, tri- or higher oligomers of 2-propenal were also detected. The conversion of 2-propenal was 55.5%, and the selectivity to (Z)-2-hexene-1,6-dial was 24.2%.

EXAMPLE 6

The same procedures as in Example 2 were followed, except for using 1.178 g (21.01 mmol) of 2-propenal, 30.9 mg (0.10 mmol) of ($\eta^4$-cyclooctadiene)($\eta^6$-cyclooctatriene)ruthenium, and 0.13 g of diethylene glycol dimethyl ether and additionally using 0.6 ml of N-methylpyrrolidinone. As a result, the reaction mixture was found to contain 0.082 g (1.46 mmol) of 2-propenal and 0.252 g (2.25 mmol) of (Z)-2-hexene-1,6-dial. In addition, tri- or higher oligomers of 2-propenal were also detected. The conversion of 2-propenal was 93.1%, and the selectivity to (Z)-2-hexene-1,6-dial was 23.0%.

EXAMPLE 7

The same procedures as in Example 2 were followed, except for using 0.691 g (12.33 mmol) of 2-propenal, 20.2 mg (0.06 mmol) of ($\eta^4$-cyclooctadiene)($\eta^5$-cyclooctatriene)ruthenium, and 0.07 g of diethylene glycol dimethyl ether and additionally using 1 ml of isopropanol. As a result, the reaction mixture was found to contain 0.191 g (3.41 mmol) of 2-propenal and 0.126 g (1.12 mmol) of (Z)-2-hexene-1,6-dial. In addition, tri- or higher oligomers of 2-propenal were also detected. The conversion of 2-propenal was 72.3%, and the selectivity to (Z)-2-hexene-1,6-dial was 25.2%.

EXAMPLE 8

The same procedures as in Example 2 were followed, except for using 0.848 g (15.13 mmol) of 2-propenal, 20.0 mg (0.06 mmol) of ($\eta^4$-cyclooctadiene)($\eta^6$-cyclooctatriene)ruthenium, and 0.1 g of diethylene glycol dimethyl ether, displacing the atmosphere in the ampule with hydrogen, and conducting the reaction for 1 hour. As a result, the reaction mixture was found to contain 0.232 g (4.13 mmol) of 2-propenal and 0.153 g (1.36 mmol) of (Z)-2-hexene-1,6-dial. In addition, tri- or higher oligomers of 2-propenal were also detected. The conversion of 2-propenal was 72.7%, and the selectivity to (Z)-2-hexene-1,6-dial was 24.8%.

EXAMPLE 9

The same procedures as in Example 8 were followed, except for using 0.790 g (14.09 mmol) of 2-propenal and replacing ($\eta^4$-cyclooctadiene)($\eta^6$-cyclooctatriene)ruthenium with 18.6 mg (0.06 mmol) of ($\eta^4$-cyclooctadiene)($\eta^6$-toluene)ruthenium. As a result, the reaction mixture was found to contain 0.233 g (4.15 mmol) of 2-propenal and 0.208 g (1.86 mmol) of (Z)-2-hexene-1,6-dial. In addition, tri- or higher oligomers of 2-propenal were also detected. The conversion of 2-propenal was 70.6%, and the selectivity to (Z)-2-hexene-1,6-dial was 37.4%.

EXAMPLE 10

In a Schlenk flask were charged 0.229 g (0.759 mmol) of ($\eta^4$-cyclooctadiene)($\eta^6$-toluene)ruthenium, 8.873 g (158.3 mmol) of 2-propenal, and, as an internal standard substance for analysis, 0.534 g of diethylene glycol dimethyl ether in a nitrogen stream. Separately, a magnetic stirring bar was put into a 30 ml-volume stainless steel autoclave, and the autoclave was maintained in a nitrogen atmosphere. The solution in the Schlenk flask was transferred to the autoclave, and the atmosphere of the autoclave was displaced with hydrogen. Hydrogen was introduced thereinto to 5 bar, and the contents were allowed to react at 70° C. for 1 hour. The reaction pressure decreased from 5.5 bar to 3.5 bar along with the reaction taking place. After completion of the reaction, the autoclave was opened, and the content was analyzed by gas chromatography. As a result, the reaction mixture was found to contain 0.521 g (9.29 mmol) of 2-propenal, 3.153 g (28.12 mmol) of (Z)-2-hexene-1,6-dial, 0.118 g (2.04 mmol) of propanal, and 0.412 g (2.45 mmol) of a trimer of 2-propenal. In addition, tetra- or higher oligomers of 2-propenal were also detected. The conversion of 2-propenal was 94.1%, and the selectivity to (Z)-2-hexene-1,6-dial was 37.8%.

EXAMPLE 11

In a 20 ml-volume glass ampule containing a magnetically stirring bar were charged 1.045 g (18.6 mmol) of 2-propenal, 0.10 g of diethylene glycol dimethyl ether, and 11.1 mg (0.039 mmol) of ($\eta^6$-benzene)($\eta^4$-cyclooctadiene)ruthenium in a nitrogen stream. The solution was allowed to react at 70° C. for 12 hours while stirring. As a result, the reaction mixture was found to contain 0.443 g (7.90 mmol) of 2-propenal, 0.186 g (1.66 mmol) of (Z)-2-hexene-1,6-dial, and 0.11 g (0.10 mmol) of trimer of 2-propenal. In addition, tetra- or higher oligomers of 2-propenal were also detected. The conversion of 2-propenal was 57.6%, and the turnover number for (Z)-2-hexene-1,6-dial was 43.0 (mol/g-atom Ru).

EXAMPLE 12

The same procedures as in Example 11 were followed except for using 1.566 g (27.9 mmol) of 2-propenal and 0.15 g of diethylene glycol dimethyl ether, and 14.9 mg (0.051 mmol) of ($\eta^6$-benzene)($\eta^4$-cyclooctadiene)ruthenium, and additionally using 1.73 ml of 1,5-cyclooctadiene. As a result, the reaction mixture was found to contain 0.515 g (9.20 mmol) of 2-propenal, 0.376 g (3.36 mmol) of (Z)-2-hexene-1,6-dial, and 0.059 g (0.35 mmol) of trimer of 2-propenal. In addition, tetra- or higher oligomers of 2-propenal were also detected. The conversion of 2-propenal was 67.1%, and the turnover number for (Z)-2-hexene-1,6-dial was 66.1 (mol/g-atom Ru).

EXAMPLE 13

The same procedures as in Example 11 were followed, except for using 1.695 g (30.2 mmol) of 2-propenal, 0.17 g of diethylene glycol dimethyl ether, 17.2 mg (0.060 mmol) of ($\eta^6$-benzene)($\eta^4$-cyclooctadiene)ruthenium and 0.314 g (2.90 mmol) of 1,5-cyclooctadiene, and conducting the reaction time for 10 hours. As a result, the reaction mixture was found to contain 0.578 g (10.32 mmol) of 2-propenal, 0.417 g (3.72 mmol) of (Z)-2-hexene-1,6-dial, and 0.079 g (0.47 mmol) of trimer of 2-propenal. In addition, tetra- or higher oligomers of 2-propenal were also detected. The conversion of 2-propenal was 65.9%, and the turnover number for (Z)-2-hexene-1,6-dial was 62.2 (mol/g-atom Ru).

EXAMPLE 14

The same procedures as in Example 11 were followed except for using 4.621 g (82.4 mmol) of 2-propenal and 0.4 g of diethylene glycol dimethyl ether, and 25.6 mg (0.089 mmol) of ($\eta^6$-benzene)($\eta^4$-cyclooctadiene)ruthenium, and 4.75 g (43.9 mmol) of 1,5-cyclooctadiene, displacing the atmosphere in the ampule with hydrogen, and conducting the reaction time for 6 hours. As a result, the reaction mixture was found to contain 2.951 g (52.65 mmol) of 2-propenal, 0.464 g (4.14 mmol) of (Z)-2-hexene-1,6-dial, and 0.167 g (0.99 mmol) of trimer of 2propenal. In addition, tetra- or higher oligomers of 2-propenal were also detected. The conversion of 2-propenal was 36.1%, and the turnover number for (Z)-2-hexene-1,6-dial was 46.5 (mol/g-atom Ru).

EXAMPLE 15 AND REFERENCE EXAMPLE 4

In an NMR sample tube were charged 0.141 g (2.51 mmol) of 2-propenal, 34.3 mg (0.119 mmol) of ($\eta^6$-benzene)($\eta^4$-cyclooctadiene)ruthenium, and 0.991 ml of a mixture of dioxane $d_8$ (98.5 atom % D) and 1,5-cyclooctadiene (1:1 volume ratio) under a nitrogen stream, and the tube was sealed. The solution was allowed to react at 70° C. in an NMR prove, and the reaction was monitored by $^1$H-NMR means. For the reference example, the same procedures were repeated except for replacing the dioxane $d_8$/1,5-cyclooctadiene solvents by dioxane-$d_8$. 2-Propenal, (Z)-2-hexene-1,6-dial, and ligands of the catalyst were quantitatively analyzed referred to a signal intensity at δ 3.55 of undeuterized dioxane. Table 1 shows results at almost same conversion of 2-propenal. Remaining Ru(COD)L represents molar percentages of ruthenium compounds possessing 1,5-cyclooctadiene ligand in charged ruthenium compound. Apparently, (Z)-2-hexene-1,6-dial formation was accelerated, and no dissociation of 1,5-cyclooctadiene ligand were observed when adding 1,5-cyclooctadiene.

TABLE 1

| | Time (h) | Conversion (%) | Turnover (mol/g-atom) | Remaining Ru(COD)$L_n$ (%) |
|---|---|---|---|---|
| Example 15 | 6 | 78.5 | 5.79 | 100 |

TABLE 1-continued

| | Time (h) | Conversion (%) | Turnover (mol/g-atom) | Remaining Ru(COD)L$_n$ (%) |
|---|---|---|---|---|
| Reference Example 4 | 15 | 77.8 | 5.57 | 78 |

EXAMPLE 16

Dimerization reaction was conducted as in Example 10, and (Z)-2-hexene-1,6-dial was isolated from the reaction mixture by distillation under reduced pressure (78° C. at 0.8 mmHg). Gas chromatographic analysis exhibited the product being 90% of purity. In a 50 ml-volume glass flask equipped with a gas burette were charged 0.132 g of 5% Pd on carbon, 1.128 g of the above (Z)-2-hexene-1,6-dial sample (containing 1.008 g (8.99 mmol) of (Z)-2-hexene-1,6-dial), and 5 ml of ethanol. The flask and the gas burette were filled up with hydrogen, and magnetically stirring was commenced at room temperature. Quantitative consumption of hydrogen was found after 6 hours. Gas chromatographic analysis showed the reaction mixture contained 0.977 g (8.56 mmol) of 1,6-hexanedial, which was assigned by NMR spectroscopy. Yield was 95.2% based on (Z)-2-hexene-1,6-dial.

REFERENCE EXAMPLE 5

Production of 1,6-hexanediamine from 1,6-hexanedial was performed by the method disclosed in JP-B-58-26902.

(1) Preparation of Schiff base of 1,6-hexanedial

In a 50 ml-volume glass flask equipped with a thermometer, a rubber septum cap, and a magnetically stirring bar were added 1.251 g (17.1 mmol) of n-butylamine and 1 ml of toluene. To this solution, 0.671 g (5.88 mmol) of 1,6-hexanedial obtained in Example 16 in toluene (1 ml) solution was added at 5° C. during 1 hour by the syringe technique. At the end of the addition, the reaction mixture was allowed to come to room temperature, and stirred for additional 3 hours to obtain colorless two layer solutions.

(2) Production of 1,6-hexanediamine

In a 30 ml-volume of an autoclave constructed of Hasteroy C were added in an argon stream 0.188 g of nickel kieselguhr catalyst (Hoechst: #52/35) and the two layer solutions obtained above. The autoclave was cooled to $-78°$ C., and 5 ml of liquid ammonia was added and sealed. Hydrogen was introduced to the reactor to reach the hydrogen pressure of 100 bar, and heating was commenced. The reaction was carried out at 120° C. for 4 hours. As the result, reaction solution was found to contain 0.533 g (4.59 mmol) of 1,6-hexanediamine by gas chromatographic analysis. Yield was 78.1% based on 1,6-hexanedial.

While the invention has been described in detail and with reference to specific examples thereof, it will be apparent to one skilled in the art that various changes and modifications can be made therein without departing from the spirit and scope thereof.

What is claimed is:

1. A process for preparing 2-hexene-1,6-dial, comprising:
   dimerizing 2-propenal in the presence of an organoruthenium dimerization catalyst.

2. A process as claimed in claim 1, wherien said dimerizing is in the presence of hydrogen.

3. A process as claimed in claim 1, wherein said dimerizing is in the presence of cyclooctadienes.

4. A process as claimed in claim 3, wherein said cyclooctadienes is 1,5-cyclooctadiene.

5. A process as claimed in claim 2, wherein said dimerizing is in the presence of cyclooctadienes.

6. A process as claimed in claim 5, wherein said cyclooctadienes is 1,5-cyclooctaidiene.

7. A process as claimed in claim 1, wherein said organoruthenium dimerization catalyst is a complex of ruthenium with an alkene, diene, triene, or an aromatic hydrocarbon compound.

8. A process as claimed in claim 1, wherein said organoruthenium compound is a member selected from the group consisting of ($\eta$hu 4-cyclooctadiene)($\eta^6$-cyclooctatriene)ruthenium, ($\eta^6$-benzene)($\eta^4$-1,3-cyclohexadiene)ruthenium, bis(ethene) ($\eta^6$-hexamethylbenzene)ruthenium, ($\eta^4$-cyclooctadiene)($\eta^6$-hexamethylbenzene)ruthenium, ($\eta^6$-benzene)($\eta^4$-cyclooctadiene)ruthenium, ($\eta^6$-benzene) ($\eta^4$-norbornadiene)ruthenium, ($\eta^4$-cyclooctadiene)($\eta^6$-1,3,5-trimethylbenzene)ruthenium, ($\eta^4$-norbornadiene)($\eta^6$-1,3,5-trimethylbenzene)ruthenium, ($\eta^4$-cyclooctadiene)($\eta^6$-toluene)ruthenium, ($\eta^4$-cyclooctadiene)($\eta^6$-xylene)ruthenium, ($\eta^6$-p-cymene)($\eta^4$-cyclooctadiene)ruthenium, ($\eta^4$-cyclooctadiene) ($\eta^6$-p-methoxybenzene)ruthenium,($\eta^4$-cyclooctadiene)($\eta^6$-cycloheptatriene)ruthenium, ($\eta^4$-cycloheptadiene)($\eta^6$-cyclopeptatriene)ruthenium, bis(cyclohexadienyl)ruthenium, and bis(hexamethylbenzene)ruthenium.

9. A process as claimed in claim 1, wherein the molar ratio of catalyst to the starting amount of 2-propenal ranges from 0.0000001 to 1:1.

10. A process as claimed in claim 9, wherein said molar ratio ranges from 0.000001 to 0.1:1.

11. A process as claimed in claim 1, wherein the temperature of reaction ranges from 0° to 200° C.

12. A process as claimed in claim 1, which reaction is conducted in the presence of hydrogen under a pressure ranging from 0.1 to 200 bar.

* * * * *